United States Patent [19]

Wright, Jr. et al.

[11] Patent Number: 4,568,685

[45] Date of Patent: Feb. 4, 1986

[54] N-[(1H-1,2,4-TRIAZOL-1-YL)ALKYL]-ARYLAMIDES

[75] Inventors: William B. Wright, Jr., Woodcliff Lake, N.J.; Jeffery B. Press, Tuxedo, N.Y.; Andrew S. Tomcufcik, Old Tappan, N.J.

[73] Assignee: American Cyanamid Company, Stamford, Conn.

[21] Appl. No.: 584,702

[22] Filed: Feb. 29, 1984

[51] Int. Cl.[4] .................... A61K 31/41; C07D 249/08; C07D 403/06

[52] U.S. Cl. .................................... 514/383; 546/94; 548/262; 548/473

[58] Field of Search ....................... 424/269; 548/262; 514/383

[56] References Cited

U.S. PATENT DOCUMENTS 4,320,134  3/1982  Iizuka et al. ...................... 548/341

FOREIGN PATENT DOCUMENTS 2854598  7/1980  Fed. Rep. of Germany ...... 424/269

OTHER PUBLICATIONS

Burger, Medicinal Chemistry, (Second Ed., New York, 1960), pp. 79–81.

Primary Examiner—Alton D. Rollins
Attorney, Agent, or Firm—M.-E. M. Timbers

[57] ABSTRACT

N-[(1H-1,2,4-Triazol-1-yl)alkyl]arylamides which are inhibitors of thromboxane synthetase enzyme.

18 Claims, No Drawings

N-[(1H-1,2,4-TRIAZOL-1-YL)ALKYL]-ARYLAMIDES

SUMMARY OF THE INVENTION

This invention relates to new organic compounds and, more particularly, is concerned with novel N-[(1H-1,2,4-triazol-1-yl)alkyl]arylamides which may be represented by the following structural formula:

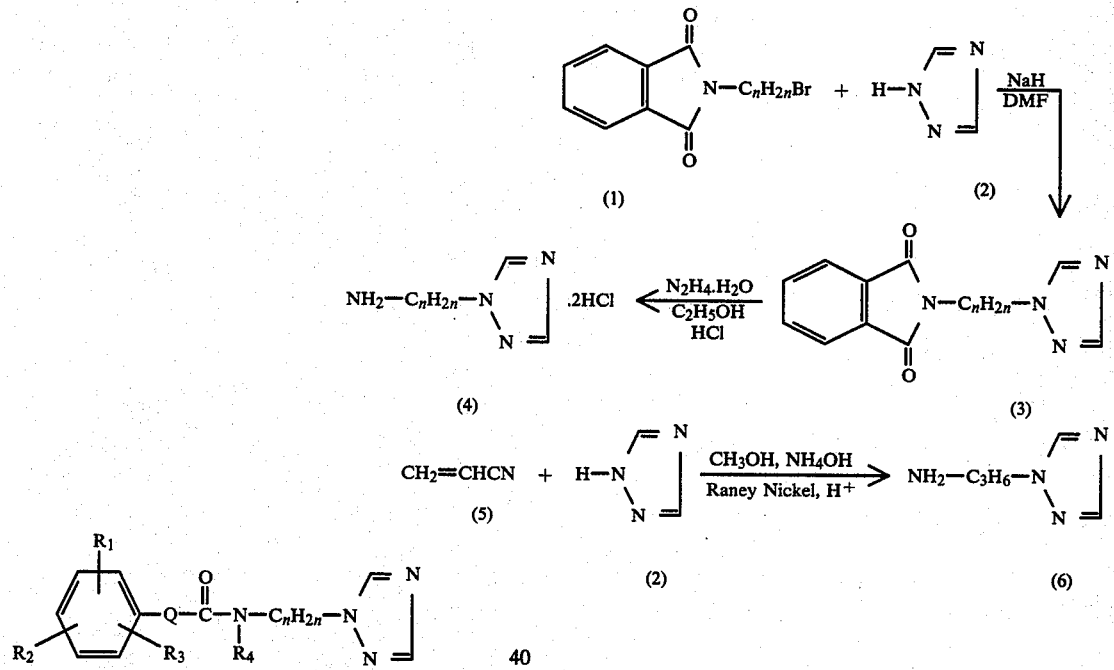

wherein $R_1$, $R_2$ and $R_3$ are each individually selected from the group consisting of hydrogen, halogen, trifluoromethyl, phenyl, straight or branched chain alkyl($C_1$-$C_6$), nitro, carboxy cyano, amino, alkylamino, dialkylamino, benzoyl, acylamino, alkoxy($C_1$-$C_3$), methylsulfonyl, methylthio and acetyl; $R_1$ and $R_2$ taken together are —(CH)$_4$—; Q is —CH=CH—, cyclopropyl, $$-C=O, -CH_2O-, \text{ or } -C_mH_{2m}-$$

where m is an integer 0–4; $R_4$ is hydrogen, alkyl($C_1$-$C_4$) or benzyl; and n is an integer 2–5, together with the pharmaceutically acceptable salts thereof.

The organic bases of this invention form nontoxic acid-addition salts with a variety of pharmacologically acceptable organic and inorganic salt-forming reagents. Thus, acid-addition salts, formed by admixture of the organic free base with one or more equivalents of an acid, suitably in a neutral solvent, are formed with such acids as sulfuric, phosphoric, hydrochloric, hydrobromic, sulfamic, citric, lactic, malic, succinic, maleic, fumaric, tartaric, acetic, benzoic, gluconic, ascorbic and the like. For purposes of this invention the free bases are equivalent to their non-toxic acid-addition salts. The acid-addition salts of the organic bases of this invention are, in general, crystalline solids, relatively soluble in water, methanol and ethanol, but relatively insoluble in non-polar organic solvents such as diethyl ether, benzene and toluene.

DETAILED DESCRIPTION OF THE INVENTION

The novel compounds of the present invention may be prepared as set forth in the following reaction schemes, wherein $R_1$, $R_2$, $R_3$, $R_4$, Q, m and n are as defined above.

METHOD I (Preparation of Intermediates)

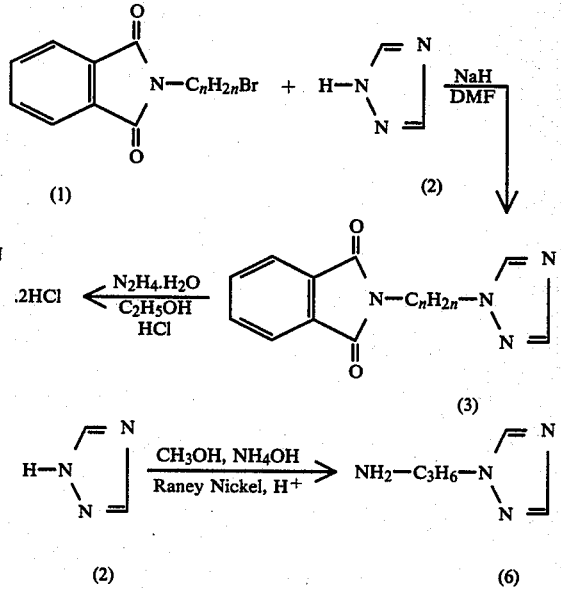

In accordance with Method I, 1H-1,2,4-triazole (2) is mixed with approximately 50% sodium hydride in dimethylformamide for about 1–3 hours, then reacted with bromoalkylphthalimide (1) with heat for about 4–8 hours giving 2-[(1H-1,2,4-triazol-1-yl)alkyl]-1H-isoindol-1,3-(2H)-dione (3), which is then reacted with hydrazine hydrate in ethanol at reflux for about 1–5 hours. Hydrochloric acid is then added and refluxing is continued for about 1–5 hours, giving the 1H-1,2,4-triazol-1-alkylamine, dihydrochloride (4).

Acrylonitrile (5) and 1H-1,2,4-triazole (2) are reacted with heat for about 2–4 hours, concentrated to an oil and then hydrogenated with Raney nickel catalyst in methanol and ammonium hydroxide for a period of about 8–10 hours, giving 1H-1,2,4-triazole-1-propanamine (6).

2-[(1H-1,2,4-Triazol-1-yl)alkyl]-1H-isoindol-1,3-(2H)-dione (3) also has utility as an antihypertensive agent and as an inhibitor of thromboxane synthetase enzyme.

METHOD II

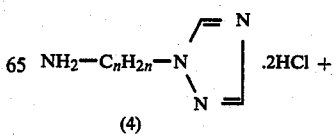

-continued

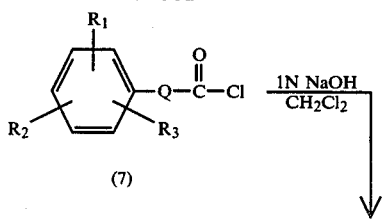
(7)

1N NaOH / CH₂Cl₂

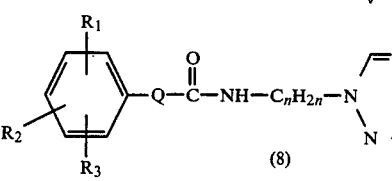
(8)

In accordance with Method II, a 1H-1,2,4-triazole-1-alkanamine, dihydrochloride (4) is reacted with an acid chloride (7), where $R_1$, $R_2$ and $R_3$ are as described above, in methylene chloride and 1N sodium hydroxide for 12–48 hours, giving the product (8).

METHOD III

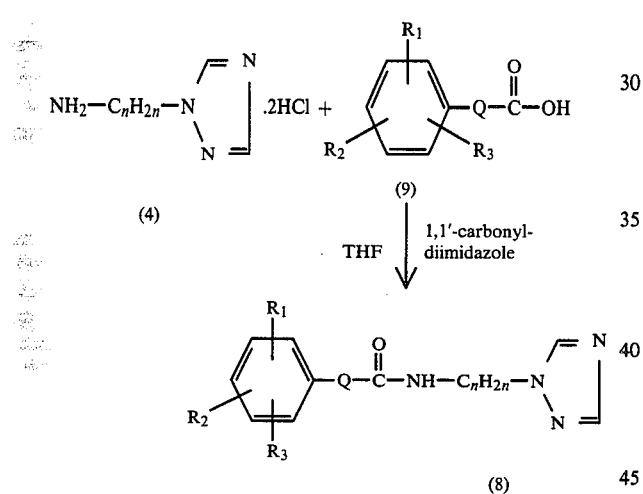

In accordance with Method III, an acid (9), where $R_1$, $R_2$ and $R_3$ are as described above, is stirred with 1,1'-carbonyldiimidazole in tetrahydrofuran for about 2–4 hours, then reacted with 1H-1,2,4-triazole-1-alkylamine dihydrochloride (4) or the corresponding free base for about 24–48 hours, giving the product (8).

METHOD IV

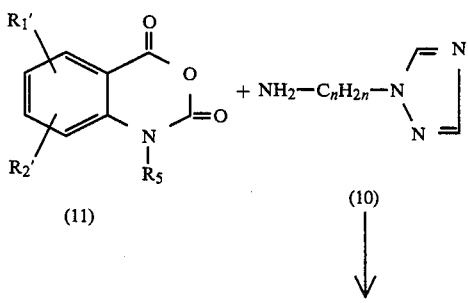

-continued

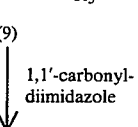
(12)

In accordance with Method IV, an isatoic anhydride (11), where $R_1'$ and $R_2'$ are each individually selected from the group consisting of hydrogen, or halogen and $R_5$ is hydrogen or lower alkyl, is condensed with a 1H-1,2,4-triazole-1-alkylamine (10) where n is an integer 2–5, giving the corresponding 2-amino-N-[ω-(1H-imidazol-1-yl)alkyl]benzamides (12). This condensation is readily carried out in an inert solvent such as benzene, toluene, xylene or dimethylsulfoxide at the reflux temperature thereof for a period of about 15 minutes to an hour or so. The product (12) precipitates from the reaction mixture or is obtained on concentration and is collected by filtration and purified.

METHOD V

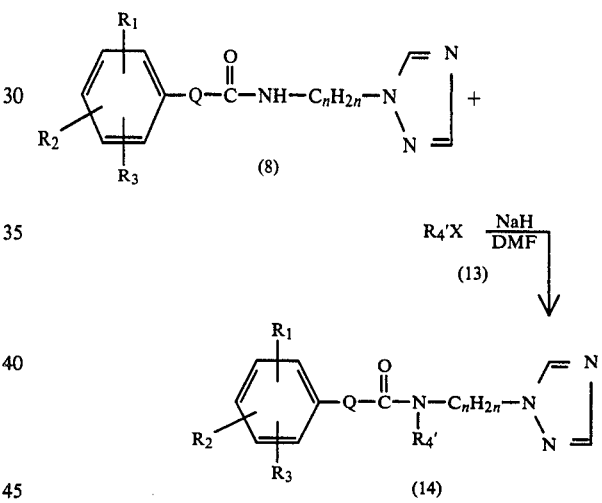

In accordance with Method V, a N-[(1H-1,2,4-triazol-1-yl)alkyl]-amide (8) is warmed with sodium hydride in dimethylformamide and then treated with an alkyl halide (13) where $R_4'$ is alkyl or benzyl and X is halogen, giving the product (14).

The compounds of this invention inhibit thromboxane synthetase enzyme. Thus, these compounds are useful in the treatment of diseases characterized by an imbalance of thromboxane $A_2$/prostacyclin such as ischemic heart disease, transient ischemic attack, thrombosis and migraine. Recent reviews have established the role of the thromboxane/prostacyclin balance in the vacular system [*Cardiovascular Diseases: New Trends in Surgical and Medical Aspects*, H. Barnett, P. Paoletti, E. Flamm and G. Brambilla, eds., Elsevier/North-Holland Biomedical Press, pp. 137–150 (1981)]. Prostacyclin ($PGI_2$) is a potent vasodilator and platelet aggregation inhibitor, whereas thromboxane ($TXA_2$) is a powerful vasoconstrictor and causative of platelet aggregation. $TXA_2$ is synthesized by thromboxane synthetase enzyme located in, for example, blood platelets. When $TXA_2$ production is increased relative to $PGI_2$, platelet aggregation, thrombosis and vasospasm may occur [Lancet (i), 1216 (1977); Lancet, 479 (1977); Science, 1135 (1976); Amer. J. Cardiology, 41, 787 (1978)]. $TXA_2$ synthetase inhibitors have been shown to have superior anti-thrombotic action to that of aspirin [J. Clin. Invest., 65, 400 (1980); Br. J. Pharmac., 76, 3 (1982)].

The role of prostaglandins, including $TXA_2$ and $PGI_2$, in ischemic heart patients has been reviewed [Cardiovacular Pharmacology of the Prostaglandins, A. G. Herman, P. M. Vanhoute, H. Denolin and A. Goosen, eds., Raven Press, New York, pp 361-374 (1982)]. Injection of $TXA_2$ into coronary arteries of guinea pigs and rabbits causes myocardial ischemia and subendocardia necrosis [Drugs of the Future, 7, 331 (1982); Proc. Jap. Acad., 53(B), 38 (1977); Eur. J. Pharmacol., 53 49 (1978)]. Recent research has demonstrated the beneficial effects of $PGI_2$ and selective inhibition of thromboxane synthetase on ischemic myocardium in canines [J. Cardiovascular Pharmacology, 4, 129 (1982)]. Thus, compounds which selectively inhibit thromboxane synthetase (and hence $TXA_2$) without adversely affecting $PGI_2$ are useful in the treatment of vascular disease such as ischemia and migraine. In addition, inhibition of $TXA_2$ formation may effectively treat platelet aggregation and prevent thrombosis.

Under urethan anesthesia, about 10 μl of arterial blood was collected in about one ml. of approximately 3.2% sodium citrate in a polystyrene tube from Okamoto-Aoki spontaneously hypertensive rats (SHR) (Taconic Farms, Germantown, N.Y.) between 19 and 24 weeks in age. The blood was diluted with about 3 ml cold saline and centrifuged at room temperature for about 15 minutes at 460xg. The platelet rich plasma (PRP) was separated. The platelets were isolated by centrifuging the PRP for about 10 minutes at 1060xg and were washed in about 4 ml of cold oxygenated Krebs phosphate buffer, pH 7.4. The chilled platelets recovered from centrifuging at about 800xg for about 10 minutes were resuspended in oxygenated Krebs phosphate buffer and diluted to contain approximately $4.5-6.0 \times 10^4$ platelets/μl.

The inhibition of thromboxane (TX) formulation was studied by determining the concentration of thromboxane $B_2$ ($TXB_2$), the stable hydrolysis product of $TXA_2$. Assay samples, prepared on ice, contained about 200 μl platelet suspension, about 50 μl saline and about 50 μl vehicle or drug under study. The samples were incubated for about 10 minutes at about 37° C. in a metabolic shaker. The reaction was terminated by immersing the tubes in an ice bath and adding about 50 μl of approximately 0.5M citric acid. The samples were centrifuged for about 10 minutes in a refrigerated centrifuge and the supernatants thus obtained were decanted and stored at about 200° C. The $TXB_2$ content for each sample was determined by a direct radioimmunoassay (RIA) utilizing a $TXB_2$ specific RIA kit purchased from New England Nuclear, Boston, MA and expressed as pg $TXB_2$ formed minute$^{-1}$ sample$^{-1}$, from which the percent inhibition of $TXB_2$ formation was calculated. The results of this test on representative compounds of this invention appear in Table I below.

TABLE I

| Compound | Dose | % Inhibition |
|---|---|---|
| 3,4-dichloro-N—[3-(1H—1,2,4-triazol-1-yl)propyl]benzamide | $10^{-4}$ | 80% |
| 4-bromo-N—[3-(1H—1,2,4-triazol-1-yl)propyl]benzamide | $10^{-4}$ | 40% |

TABLE I-continued

| Compound | Dose | % Inhibition |
|---|---|---|
| 4-chloro-N—[3-(1H—1,2,4-triazol-1-yl)propyl]benzamide | $10^{-4}$ | 16% |
| 4-iodo-N—[3-(1H—1,2,4-triazol-1-yl)propyl]benzamide | $10^{-4}$ | 82% |
| 4-acetyl-N—[3-(1H—1,2,4-triazol-1-yl)propyl]benzamide | $10^{-4}$ | 52% |
| 3-(4-chlorophenyl)-N—[3-(1H—1,2,4-triazol-1-yl)propyl]-2-propenamide | $10^{-4}$ | 47% |
| 4-(methylthio)-N—[3-(1H—1,2,4-triazol-1-yl)propyl]benzamide | $10^{-4}$ | 71% |
| 4-bromo-N—[4-(1H—1,2,4-triazol-1-yl)butyl]benzamide | $10^{-4}$ | 88% |
| 4-methyl-N—[3-(1H—1,2,4-triazol-1-yl)propyl]benzamide | $10^{-4}$ | 66% |
| 3-fluoro-N—[3-(1H—1,2,4-triazol-1-yl)propyl]benzamide | $10^{-4}$ | 82% |
| 4-cyano-N—[3-(1H—1,2,4-triazol-1-yl)propyl]benzamide | $10^{-4}$ | 12% |
| 4-methoxy-N—[3-(1H—1,2,4-triazol-1-yl)propyl]benzamide | $10^{-4}$ | 71% |
| 4-(methylsulfonyl)-N—[3-(1H—1,2,4-triazol-1-yl)]benzamide | $10^{-4}$ | 26% |
| N—[4-(1H—1,2,4-triazol-1-yl)butyl]-1-naphthalene acetamide, fumarate | $10^{-4}$ | 88% |
| N—[4-(1H—1,2,4-triazol-1-yl)butyl]-[1,1'-biphenyl]-2-carboxamide, fumarate | $10^{-4}$ | 89% |
| 3,4-dichloro-N—[4-(1H—1,2,4-triazol-1-yl)butyl]benzamide | $10^{-4}$ | 82% |
| 4-fluoro-N—[3-(1H—1,2,4-triazol-1-yl)propyl]benzamide | $10^{-4}$ | 67% |
| 3,4,5-trimethoxy-N—[3-(1H—1,2,4-triazol-1-yl)propyl]benzamide | $10^{-4}$ | 64% |
| 4-(acetylamino)-N—[3-(1H—1,2,4-triazol-1-yl)propyl]benzamide | $10^{-4}$ | 75% |
| 4-benzoyl-N—[3-(1H—1,2,4-triazol-1-yl)propyl]benzamide | $10^{-4}$ | 65% |
| N—[3-(1H—1,2,4-triazol-1-yl)propyl]-[1,1'-biphenyl]-2-carboxamide, fumarate | $10^{-4}$ | 65% |
| 4-(1,1-dimethylethyl)-N—[3-(1H—1,2,4-triazol-1-yl)propyl]benzamide | $10^{-4}$ | 86% |
| 3-nitro-N—[3-(1H—1,2,4-triazol-1-yl)propyl]benzamide | $10^{-4}$ | 72% |
| 3-chloro-N—[3-(1H—1,2,4-triazol-1-yl)propyl]benzamide | $10^{-4}$ | 86% |
| 3-bromo-N—[3-(1H—1,2,4-triazol-1-yl)propyl]benzamide | $10^{-4}$ | 85% |
| 2-[4-(1H—1,2,4-triazol-1-yl)-butyl]-1H—isoindol-1,3-(2H)—dione | $10^{-4}$ | 70% |
| 2-[5-(1H—1,2,4-triazol-1-yl)-pentyl]-1H—isoindol-1,3-(2H)—dione | | 79% |

Hypotensive Activity in Spontaneously Hypertensive Rats

The novel compounds of the present invention are active hypotensive agents and were tested for hypotensive activity by the method of P. S. Chan and D. Poorvin, Clinical and Experimental Hypertension, 1 (6), 817-830 (1979). Male, 16 week old, spontaneously hypertensive rats of the Okamoto strain, from Taconic Farms, Germantown, N.Y., having an average mean arterial blood pressure of 170 ±1.5 mm of mercury are used in the test. One to 3 rats are used per test compound. A rat is dosed by gavage with a test compound, suspended in approximately 2% pre-boiled starch at a concentration of about 50 mg/ml, at a dose of about 100 mg/kg of body weight or less, with approximately 0.9% sodium chloride loading at a dose of about 25 ml/kg of body weight. A second identical dose of the test compound, without sodium chloride loading, is given about 24 hours later. At about 28 hours after the initial dose the mean arterial blood pressure is measured by the method of Chan and Poorvin vide supra. The procedure is repeated in a second and third rat when necessary.

TABLE II

| Compound | MABP/mm Hg (No. of Rats) |
| --- | --- |
| 3,4-dichloro-N—[3-(1H—1,2,4-triazol-1-yl)propyl]benzamide | 150 (1) |
| 4-bromo-N—[3-(1H—1,2,4-triazol-1-yl)-propyl]benzamide | 147 (2) |
| 4-iodo-N—[3-(1H—1,2,4-triazol-1-yl)-propyl]benzamide | 128 (3) |
| 3-(4-chlorophenyl)-N—[3-(1H—1,2,4-triazol-1-yl)propyl]-2-propenamide | 137 (3) |
| 4-bromo-N—[4-(1H—1,2,4-triazol-1-yl)-butyl]benzamide | 137 (3) |
| 4-methyl-N—[3-(1H—1,2,4-triazol-1-yl)-propyl]benzamide | 145 (2) |
| 4-cyano-N—[3-(1H—1,2,4-triazol-1-yl)-propyl]benzamide | 119 (2) |
| 4-(dimethylamino)-N—[3-(1H—1,2,4-triazol-1-yl)propyl)]benzamide | 117 (2) |
| N—[4-(1H—1,2,4-triazol-1-yl)butyl]-1-naphthaleneacetamide, fumarate | 134 (3) |
| N—[4-(1H—1,2,4-triazol-1-yl)butyl]-[1,1'-biphenyl]-2-carboxamide, fumarate | 145 (3) |
| 3,4-dichloro-N—[4-(1H—1,2,4-triazol-1-yl)butyl]benzamide | 141 (2) |
| 4-t-butyl-N—[3-(1H—1,2,4-triazol-1-yl)propyl]benzamide | 123 (3) |
| N—[3-(1H—1,2,4-triazol-1-yl)propyl]benzamide | 124 (3) |
| 4-(methylsulfonyl)-N—[3-(1H—1,2,4-triazol-1-yl)propyl]benzamide | 110 (1) |
| 2-[4-(1H—1,2,4-triazol-1-yl)-butyl]-1H—isoindol-1,3-(2H)—dione | 119 (4) |

The novel compounds of the present invention have been found to be highly useful for inhibiting thromboxane synthetase in mammals when administered in amounts ranging from about 0.1 mg to about 20.0 mg/kg of body weight per day. A preferred dosage regimen for optimum results would be from about 0.5 mg to about 10.0 mg/kg of body weight per day. Such dosage units are employed that a total of from about 35 to about 700 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular, or subcutaneous routes.

Compositions according to the present invention having the desired clarity, stability and adaptability for parenteral use are obtained by dissolving from 0.10% to 10.0% by weight of active compound in a vehicle consisting of a polyhydric aliphatic alcohol or mixtures thereof. Especially satisfactory are glycerin, propylene glycol, and polyethylene glycols. The polyethylene glycols consist of a mixture of non-volatile, normally liquid, polyethylene glycols which are soluble in both water and organic liquids and which have a molecular weight of from about 200 to 1500. Although the amount of active compound dissolved in the above vehicle may vary from 0.10% to 10.0% by weight, it is preferred that the amount of active compound employed be from about 3.0% to about 9.0% by weight. Although various mixtures of the aforementioned non-volatile polyethylene glycols may be employed, it is preferred to use a mixture having an average molecular weight of from about 200 to about 400.

In addition to the active compound, the parenteral solutions may also contain various preservatives which may be used to prevent bacterial and fungal contamination. The preservatives which may be used for these purposes are, for example, myristyl-gamma-picolinium chloride, benzalkonium chloride, phenethyl alcohol, p-chlorophenyl-α-glycerol ether, methyl and propyl parabens, and thimerosal. As a practical matter, it is also convenient to employ antioxidants. Suitable antioxidants include, for example, sodium bisulfite, sodium metabisulfite, and sodium formaldehyde sulfoxylate. Generally, from about 0.05% to about 0.2% concentrations of antioxidant are employed.

For intramuscular injection, the preferred concentration of active compound is 0.25 to 0.50 mg/mg of the finished compositions. The novel compounds of the present invention are equally adapted to intravenous administration when diluted with water or diluents employed in intravenous therapy such as isotonic glucose in appropriate quantities. For intravenous use, initial concentrations down to about 0.05 to 0.25 mg/ml of active ingredient are satisfactory.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: a binder such as gum tragacanth, acacia, corn starch or gelatin; excipients such as dicalcium phosphate, a disintegrating agent such as corn starch, potato starch, aliginic acid and the like; a lubricant such as magnesium stearate; and a sweetening agent such as sucrose, lactose or saccharin may be added or a flavoring agent such a peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The following specific examples illustrate the preparation of the compounds of the present invention.

EXAMPLE 1

1H-1,2,4-Triazole-1-butanamine, dihydrochloride

A mixture of about 9.0 g of 1H-1,2,4-triazole, about 6.24 g of approximately 50% sodium hydride in oil and about 130 ml of dimethylformamide was stirred for about 1.5 hours, then about 33 g of N-(4-bromobutyl)phthalimide was added and this mixture was heated on a steam bath for about 6 hours then concentrated to a solid residue. Water and methylene chloride were added, the organic layer was separated, washed with water, dried and concentrated to a residue. This residue was crystallized from ethanol, giving about 27.3 g of 2-[4-(1H-1,2,4-triazol-1-yl)butyl]-1H-isoindol-1,3(2H)-dione.

A mixture of about 27 g of the above dione, about 4.85 of hydrazine hydrate and about 250 ml of ethanol was refluxed for about 3 hours and then cooled. An about 450 ml portion of 3N hydrochloric acid was added and the mixture was refluxed for about 3 hours, the concentrated to ½ volume and filtered. The filtrate was concentrated to a solid which was reconcentrated twice from ethanol, giving about 18.2 g of the desired intermediate as white crystals, mp 183°–186° C.

EXAMPLE 2

1H-1,2,4-Triazole-1-ethanamine, dihydrochloride

A mixture of about 25.4 g of N-(2-bromoethyl)phthalimide, about 10.0 g of sodium triazole and about 300 ml of dimethylformamide was heated on a steam bath for about 3 hours and then concentrated. The residue was heated twice on a steam bath with a total of about 400 ml of toluene, filtered and then cooled, giving about 10.1 g of 2-[4-(1H-1,2,4-triazol-1-yl)ethyl]-1H-isoindol-1,3(2H)-dione.

A mixture of about 7.5 g of the above dione, about 1.70 ml of hydrazine hydrate and about 120 ml of ethanol was refluxed for about 3 hours, then cooled and about 160 ml of approximately 3N hydrochloric acid was added. This mixture was refluxed for about 2 hours, then concentrated, water was added and the mixture filtered. The filtrate was concentrated and the residue recrystallized twice from ethanol, giving about 6.1 g of the desired intermediate as a white solid, mp 200°–210° C.

EXAMPLE 3

1H-1,2,4-Triazole-1-propanamine

A mixture of about 20.7 of 1H-1,2,4-triazole and about 37.5 ml of acrylonitrile was heated on a steam bath for about 3 hours and then concentrated to an oil. This oil was added to about 200 ml of methanol and about 100 ml of concentrated ammonium hydroxide containing Raney nickel catalyst in a Paar apparatus and hydrogenated for about 8¼ hours with an uptake of about 46 psi of hydrogen. The catalyst was removed by filtration and ethanol was added to the filtrate. The mixture was filtered, the filtrate was concentrated, then reconcentrated from toluene, giving about 36.6 g of the desired intermediate as an oil.

EXAMPLE 4

1H-1,2,4-Triazole-1-pentanamine

A mixture of about 5.92 g of N-(5-bromopentyl)phthalimide, about 2.07 g of sodium triazole and about 25 ml of dimethylformamide was heated in an oil bath at about 100° C. for about 9 hours and then concentrated to remove the solvent. Methylene chloride was added and the insoluble material removed by filtration. The methylene chloride layer was washed with water, dried and concentrated. The residue was treated with ethanolic hydrochloric acid and ether and the crystalline material recovered by filtration. On recrystallization from ethanol, 2-[5-(1H-1,2,4-triazole-1-yl)pentyl]-1H-isoindol-1,3(2H)-dione, hydrochloride, mp 185°–188° C. was obtained.

A mixture of about 7.4 g of the above dione, about 2.2 g of sodium carbonate and about 10 ml of water was stirred and methylene chloride was added. The layers were separated and the organic layer dried and concentrated to remove the solvent. The residual oil, about 1.0 ml of hydrazine hydrate and about 80 ml of ethanol were refluxed for about 3 hours, cooled and about 100 ml of approximately 3N hydrochloric acid was added. This mixture was refluxed for about 2 hours, concentrated, water was added and the mixture was filtered. The filtrate was concentrated to remove volatile material and the crude dihydrochloride salt was treated with saturated potassium carbonate solution and extracted with methylene chloride. The organic layer was dried on magnesium sulfate and concentrated to obtain the desired product as an oil.

EXAMPLE 5

3,4-Dichloro-N-[4-(1H-1,2,4-triazol-1-yl)butyl]benzamide

A mixture of about 2.13 g of 1H-1,2,4-triazole-1-butanamine, dihydrochloride, about 75 ml of methylene chloride, about 30 ml of approximately 1N sodium hydroxide and about 1.41 ml of 3,4-dichlorobenzoyl chloride was stirred at room temperature overnight. An additional, about 5 ml of approximately 1N sodium hydroxide and about 50 ml of methylene chloride were added and the layers were separated. The organic layer was washed with water, dried and concentrated. The oil was collected and crystallized from ether, giving about 2.3 g of the desired product as white crystals, mp 97°–99° C.

Following the procedure of Example 5 and using appropriate acid chlorides, the products of Examples 6–11, found in Table III, were obtained, either as the free base or as an acid addition salt.

TABLE III

| Example | Acid Chloride | Product | MP °C. |
|---|---|---|---|
| 6 | 2-phenylbenzoyl chloride | N—[4-(1H—1,2,4-triazol-1-yl)butyl] [1,1'-biphenyl]-2-carboxamide, fumarate | 110–112 |
| 7 | naphthoyl-chloride | N—[4-(1H—1,2,4-triazol-1-yl)butyl]-1-naphthalene carboxamide fumarate | 72–75 |
| 8 | 4-bromobenzoyl chloride | 4-bromo-N—[4-(1H—1,2,4-triazol-1-yl)butyl] benzamide | 125–127 |
| 9 | 3-chlorobenzoyl chloride | 3-chloro-N—[4-(1H—1,2,4-triazol-1-yl)butyl]benzamide | 67–68 |
| 10 | 4-chlorobenzoyl chloride | 4-chloro-N—[4-(1H—1,2,4-triazol-1-yl)butyl]benzamide | 87–88 |
| 11 | 4-trifluoromethyl benzoyl chloride | 4-trifluoromethyl-N—[4-(1H—1,2,4-triazol-1-yl)-butyl]benzamide | 118–120 |

EXAMPLE 12

3,4-Dichloro-N-[3-(1H-1,2,4-triazol-1-yl)propyl]benzamide

A mixture of about 3.78 g of 1H-1,2,4-triazole-1-propanamine and about 33 ml of approximately 1N sodium hydroxide in about 100 ml of methylene chloride was stirred. An about 6.9 g portion of 3,4-dichlorobenzoyl chloride was added, the mixture was stirred about 6 hours, then allowed to stand overnight. An about 10 ml portion of approximately 1N sodium hydroxide and about 100 ml of methylene chloride were added and the mixture was shaken, then allowed to separate. The organic layer was washed with two about 40 ml portions of water, dried, filtered and evaporated to a solid which was crystallized from ethyl acetate, giving about 5.0 g of the desired product as off-white crystals, mp 128°–130° C.

Following the procedure of Example 12 and using appropriate acid chlorides, the products of Examples 13–26, found in Table IV, were obtained, either as the free base or as an acid-addition salt.

TABLE IV

| Example | Acid Chloride | Product | MP °C. |
|---|---|---|---|
| 13 | t-butylbenzoyl chloride | 4-(1,1-dimethylethyl)-N—[3-(1H—1,2,4-triazol-1-yl)propyl]benzamide | 90–91 |
| 14 | 3-nitrobenzoyl chloride | 3-nitro-N—[3-(1H—1,2,4-triazol-1-yl)propyl]benzamide | 101–103 |
| 15 | 3-chlorobenzoyl chloride | 3-chloro-N—[3-(1H—1,2,4-triazol-1-yl)propyl]benzamide | 57–60 (dec.) |
| 16 | 4-fluorobenzoyl chloride | 4-fluoro-N—[3-(1H—1,2,4-triazol-1-yl)propyl]benzamide | 100–101 |
| 17 | naphthoyl chloride | N—[3(1H—1,2,4-triazol-1-yl)propyl]-1-naphthalenecarboxamide, fumarate | 105–107 |
| 18 | 2-phenylbenzoyl chloride | N—[3-(1H—1,2,4-triazol-1-yl)propyl] [1,1'-biphenyl]-2-carboxamide, fumarate | 50–53 |
| 19 | 4-cyanobenzoyl chloride | 4-cyano-N—[3-(1H—1,2,4-triazol-1-yl)propyl]benzamide | 145–147 |
| 20 | 3-fluorobenzoyl chloride | 3-fluoro-N—[3-(1H—1,2,4-triazol-1-yl)propyl]benzamide | 94–96 |
| 21 | 4-toluoyl chloride | 4-methyl-N—[3-(1H—1,2,4-triazol-1-yl)propyl]benzamide | 76–78 |
| 22 | 4-chlorobenzoyl chloride | 4-chloro-N—[3-(1H—1,2,4-triazol-1-yl)propyl]benzamide | 110–112 |
| 23 | 4-bromobenzoyl chloride | 4-bromo-N—[3-(1H—1,2,4-triazol-1-yl)propyl]benzamide | 115–117 |
| 24 | benzoyl chloride | N—[3-(1H—1,2,4-triazol-1-yl)propyl]benzamide | 75–78 |
| 25 | 3-trifluoromethylbenzoyl chloride | 3-trifluoromethyl-N—[3-(1H—1,2,4-triazol-1-yl)propyl]benzamide hydrochloride | 160–162 |
| 26 | 4-trifluoromethyl benzoyl chloride | 4-trifluoromethyl-N—[3-(1H—1,2,4-triazol-1-yl)propyl]benzamide hydrochloride | 180–182 |

EXAMPLE 27

4-Iodo-N-[3-(1H-1,2,4-triazol-1-yl)propyl]benzamide

A mixture of about 2.48 g of 4-iodobenzoic acid, about 1.62 g of 1,1'-carbonyldiimidazole and about 30 ml of tetrahydrofuran was stirred for about 3 hours, then about 1.3 ml of 1H-1,2,4-triazole-1-propanamine was added and stirring was continued overnight. The mixture was heated for about 2 hours, about 5 ml of water was added, heating was continued for an additional hour then the mixture was concentrated to a residue. Methylene chloride and about 10 ml of approximately 1N sodium hydroxide were added. The organic layer was separated, washed with water, dried and concentrated, giving about 2.7 g of the desired product as a white solid, mp 132°–134° C.

Following the procedure of Example 27 and using appropriate acids, the products of Examples 28–45, found in Table V, were obtained.

TABLE V

| Example | Acid | Product | MP °C. |
|---|---|---|---|
| 28 | 4-acetylbenzoic acid | 4-acetyl-N—[3-(1H—1,2,4-triazol-1-yl)propyl]benzamide | 100–102 |
| 29 | 4-chlorocinnamic acid | 3-(4-chlorophenyl)-N—[3-(1H—1,2,4-triazol-1-yl)propyl]-2-propenamide | 124–126 |
| 30 | 4-methylthiobenzoic acid | 4-(methylthio)-N—[3-(1H—1,2,4-triazol-1-yl)propyl]benzamide | 106–108 (dec) |
| 31 | 4-methoxybenzoic acid | 4-methoxy-N—[3-(1H—1,2,4-triazol-1-yl)propyl]benzamide | 120–122 |
| 32 | 4-methylsulfonylbenzoic acid | 4-(methylsulfonyl)-N—[3-(1H—1,2,4-triazol-1-yl)propyl]benzamide | 152–153 |
| 33 | 3,4,5-trimethoxybenzoic acid | 3,4,5-trimethoxy-N—[3-(1H—1,2,4-triazol-1-yl)propyl]benzamide | 128–129 |
| 34 | 4-acetamidobenzoic acid | 4-(acetylamino)-N—[3-(1H—1,2,4-triazol-1-yl)propyl]benzamide | 186–187 |
| 35 | 4-benzoylbenzoic acid | 4-benzoyl-N—[3-(1H—1,2,4-triazol-1-yl)propyl]benzamide | 143–145 |
| 36 | 3-bromobenzoic acid | 3-bromo-N—[3-(1H—1,2,4-triazol-1-yl)propyl]benzamide | 70–73 |
| 37 | 4-dimethylaminobenzoic acid | 4-(dimethylamino)-N—[3-(1H—1,2,4-triazol-1-yl)propyl]benzamide | 132–134 |
| 38 | 3-chlorophenyl acetic acid | 2-(3-chlorophenyl)-N—[3-(1H—1,2,4-triazol-1-yl)propyl]acetamide, hydrochloride | 146–152 |
| 39 | 4-phenylbutyric acid | 4-phenyl-N—[3-(1H—1,2,4-triazol-1-yl)propyl]butyramide | oil |
| 40 | 4-chlorophenoxy acetic acid | 2-(4-chlorophenoxy)-N—[3-(1H—1,2,4-triazol-1-yl)propyl acetamide | 74–76 |
| 41 | 4-butoxybenzoic acid | 4-butoxy-N—[3-(1H—1,2,4-triazol-1-yl)propyl]benzamide | 83–85 |
| 42 | 2-fluorobenzoic acid | 2-fluoro-N—[3-(1H—1,2,4-triazol-1-yl)propyl]benzamide, hydrochloride | 166–168 |
| 43 | phenylgloxylic acid | N—[3-(1H—1,2,4-triazol-1-yl)propyl]-2-oxobenzenenacetamide | oil |
| 44 | 2-phenylcyclopropane-1-carboxylic acid | 2-phenyl-N—[3-(1H—1,2,4-triazol-1-yl)propyl]cyclopropane carboxamide | 99–101 |
| 45 | 1-phenyl-1-cyclopropane carboxylic acid | 1-phenyl-N—[3-(1H—1,2,4-triazol-1-yl)propyl]cyclopropane carbox- | 123–126 |

TABLE V-continued

| Example | Acid | Product | MP °C. |
|---|---|---|---|
|  |  | amide, hydrochloride |  |

EXAMPLE 46

4-Bromo-N-[2-(1H-1,2,4-triazol-1-yl)ethyl]benzamide

A mixture of about 2.2 g of 4-bromobenzoyl chloride, about 1.85 g of 1H-1,2,4-triazole-1-ethanamine dihydrochloride, about 30 ml of approximately 1N sodium hydroxide and about 75 ml of methylene chloride was stirred overnight, then about 5 ml of approximately 1N sodium hydroxide and about 75 ml of methylene chloride were added. The layers were separated and the organic layer was concentrated to remove the solvent. The crystalline residue was washed onto a filter with ether giving the desired product, mp 160°–162° C.

EXAMPLE 47

4-Chloro-N-[5-(1H-1,2,4-triazol-1-yl)pentyl]benzamide

A mixture of about 2.30 g of 1H-1,2,4-triazole-1-pentanamine dihydrochloride, about 75 ml of methylene chloride, about 30 ml of approximately 1N sodium hydroxide and about 1.2 ml of 4-chloro benzoyl chloride was stirred for about 18 hours, then about 5 ml of approximately 1N sodium hydroxide and about 50 ml of methylene chloride were added and the layers were separated. The organic layer was washed with water dried and concentrated, giving the desired product, mp 68°–70° C.

EXAMPLE 48

4-Bromo-N-[5-(1H-1,2,4-triazol-1-yl)pentyl]benzamide

When 4-bromobenzoyl chloride is substituted for 4-chlorobenzoyl chloride in the procedure of Example 47, the desired compound, mp 93°–95° C. is obtained.

EXAMPLE 49

2-Carboxy-N-[3-(1H-1,2,4-triazol-1-yl)propyl]benzamide

A solution of about 4.44 g of phthalic anhydride in about 75 ml of methylene chloride was treated with a solution of about 3.78 g of 1H-1,2,4-triazole-1-pentanamine in about 25 ml of chloroform. Precipitation occurred. After about 2 hours, the precipitate was recovered by filtration and then recrystallized from ethanol. The desired product melted at about 162°–164° C.

EXAMPLE 50

2-Amino-N-[3-(1H-1,2,4-triazol-1-yl)propyl]benzamide

A mixture of about 2.5 g of 1H-1,2,4-triazole-1-propanamine, about 3.26 g of isatoic anhydride and about 20 ml of ethanol was heated in an oil bath at about 70° C. for about 30 minutes and then concentrated. The residue was recrystallized from ethyl acetate and the desired product, mp 96°–98° C., was obtained.

EXAMPLE 51

2-Methylamino-N-[3-(1H-1,2,4-triazol-1-yl)propyl]benzamide

When N-methylisatoic anhydride is substituted for isatoic anhydride in the procedure of Example 50, the desired compound, mp 131°–133° C. is obtained.

EXAMPLE 52

2-Amino-5-chloro-N-[3-(1H-1,2,4-triazol-1-yl)propyl]benzamide

The desired compound, mp 93°–95° C., is obtained when 5-chloroisatoic anhydride is substituted for isatoic anhydride in the procedure of Example 50.

EXAMPLE 53

4-Bromo-2-[3-(1H-1,2,4-triazol-1-yl)propyl]-1H-isoindol-1,3(2H)-dione

A mixture of about 2.27 g of 4-bromo-phthalic anhydride and about 1.25 g of 3-(1H-1,2,4-triazol-1-yl)propanamine is heated to about 155°–165° C. for approximately 45 minutes, and then boiled with about 50 ml of toluene. The reaction mixture is then allowed to cool to about 25° C., and then filtered to remove insoluble material. The toluene layer is concentrated to remove the solvent and the residue is recrystallized from ethanol to obtain the desired compound mp 113°–115° C.

EXAMPLE 54

4-Bromo-2-[5-(1H-1,2,4-triazol-1-yl)pentyl]-1H-isoindol-1,3(2H)-dione

When 4-bromophthalic anhydride is reacted with 5-(1H-1,2,4-triazol-1-yl) pentanamine by the procedure of Example 53, the desired compound, mp 102°–104° C., is obtained.

EXAMPLE 55

4,5-Dichloro-2-[5-(1H-1,2,4-triazol-1-yl)propyl]-1H-isoindol-1,3(2H)-dione

The desired compound, mp 148°–150° C., is obtained when 4,5-dichlorophthalic anhydride is substituted for 4-bromo-phthalic anhydride in the procedure of Example 53.

EXAMPLE 56

4,5-Dichloro-2-[5-(1H-1,2,4-triazol-1-yl)pentyl]-1H-isoindol-1,3(2H)-dione

The desired compound, mp 105°–106° C., is obtained when 4,5-dichlorophthalic anhydride and 5-(1H-1,2,4-triazol-1-yl)pentanamine are reacted by the procedure of Example 53.

What is claimed is:

1. A compound having the formula:

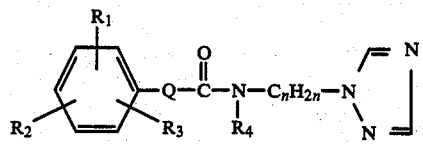

wherein $R_1$, $R_2$ and $R_3$ are each individually selected from the group consisting of hydrogen, halogen, trifluoromethyl, phenyl, straight or branched chain alkyl($C_1$–$C_6$), nitro, carboxy, cyano, amino, methylamino, dimethylamino, benzoyl, acetamido, alkoxy($C_1$–$C_3$), methylsulfonyl, methylthio and acetyl; $R_1$ and $R_2$ taken together are —(CH)$_4$—; Q is —CH=CH—, cyclopropyl,

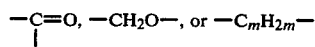

where m is an integer 0–4; $R_4$ is hydrogen, alkyl($C_1$–$C_4$) or benzyl; and n is an integer 2–5, and the pharmaceutically acceptable salts thereof.

2. The compound according to claim 1, 4-t-butyl-N-[3-(1H-1,2,4-triazol-1-yl)propyl]benzamide.

3. The compound according to claim 1, 4-iodo-N-[3-(1H-1,2,4-triazol-1-yl)propyl]benzamide.

4. The compound according to claim 1, 4-cyano-N-[3-(1H-1,2,4-triazol-1-yl)propyl]benzamide.

5. The compound according to claim 1, 3-fluoro-N-[3-(1H-1,2,4-triazol-1-yl)propyl]benzamide.

6. The compound according to claim 1, N-[4-(1H-1,2,4-triazol-1-yl)butyl]-1-naphthaleneacetamide, fumarate.

7. The compound according to claim 1, N-[3(3H-1,2,4-triazol-1-yl)propyl]benzamide.

8. The compound according to claim 1, 3,4-dichloro-N-[4-(1H-1,2,4-triazol-1-yl)butyl]benzamide.

9. The compound according to claim 1, 4-(1,1-dimethylethyl)-N-[3-(1H-1,2,4-triazol-1-yl)propyl]benzamide.

10. The compound according to claim 1, 3-chloro-N-[3-(1H-1,2,4-triazol-1-yl)propyl]benzamide.

11. The compound according to claim 1, 3-bromo-N-[3-(1H-1,2,4-triazol-1-yl)propyl]benzamide.

12. The compound according to claim 1, 4(dimethylamino)-N-[3-(1H-1,2,4-triazol-1-yl)propyl]benzamide.

13. The compound according to claim 1, 4-(methylsulfonyl)-N-[3-(1H-1,2,4-triazol-1-yl)propyl]benzamide.

14. The compound according to claim 1, 3,4,5-trimethoxy-N-[3-(1H-1,2,4-triazol-1-yl)propyl]benzamide.

15. The compound according to claim 1, 4-fluoro-N-[3-(1H-1,2,4-triazol-1-yl)propyl]benzamide.

16. A method of inhibiting thromboxane synthetase enzyme in a mammal which comprises administering to said mammal an effective amount of a compound as recited in claim 1.

17. A thromboxane synthetase enzyme inhibiting composition of matter in dosage unit form comprising from about 10 mg to about 700 mg of a compound as recited in claim 1 in association with a pharmaceutically acceptable carrier.

18. A method of inhibiting hypertension in a mammal which comprises administering to said mammal an effective amount of a compound as recited in claim 1.

* * * * *